(12) United States Patent
Schwartz et al.

(10) Patent No.: US 8,372,435 B2
(45) Date of Patent: Feb. 12, 2013

(54) MODULAR MONOLAYER COATINGS FOR SELECTIVE ATTACHMENT OF NANOPARTICLES TO BIOMOLECULES

(75) Inventors: Jeffrey Schwartz, Princeton, NJ (US); Christopher A. Traina, Napa, CA (US); Thomas Joseph Dennes, Parksburg, PA (US)

(73) Assignee: Princeton University, Princeton, NJ (US)

( * ) Notice: Subject to any disclaimer, the term of this patent is extended or adjusted under 35 U.S.C. 154(b) by 549 days.

(21) Appl. No.: 12/489,242

(22) Filed: Jun. 22, 2009

(65) Prior Publication Data

US 2010/0034742 A1 Feb. 11, 2010

Related U.S. Application Data

(60) Provisional application No. 61/075,002, filed on Jun. 23, 2008.

(51) Int. Cl.
*A61K 9/51* (2006.01)
*C01F 17/00* (2006.01)

(52) U.S. Cl. ........ 424/489; 420/416; 977/773; 977/902; 977/904; 977/908; 977/911; 977/927

(58) Field of Classification Search .................. None
See application file for complete search history.

(56) References Cited

U.S. PATENT DOCUMENTS

| | | |
|---|---|---|
| 2003/0180780 A1 | 9/2003 | Feng et al. |
| 2004/0023048 A1 | 2/2004 | Schwartz et al. |
| 2005/0176863 A1 | 8/2005 | Yokota et al. |
| 2006/0241008 A1 | 10/2006 | Baker et al. |
| 2007/0009436 A1* | 1/2007 | Rondinone et al. .......... 424/1.69 |
| 2007/0111971 A1 | 5/2007 | Eaddy, III et al. |
| 2007/0249943 A1 | 10/2007 | Texier-Nogues et al. |
| 2007/0258889 A1 | 11/2007 | Douglas et al. |
| 2008/0089836 A1 | 4/2008 | Hainfeld |

FOREIGN PATENT DOCUMENTS

WO  WO 2006124670 A2 * 11/2006

OTHER PUBLICATIONS

L Qi, A Sehgal, JC Castaing, JP Chapel, J Fresnais, JF Berret, F Cousin. "Redispersible Hybrid Nanopowders: Cerium Oxide Nanoparticle Complexes with Phosphonated-PEG Oligomers." ACS Nano, vol. 2 No. 5, 2008, pp. 879-888, Published May 3, 2008.*
CA Traina, J Schwartz. "Surface Modification of Y2O3 Particles." Langmuir, vol. 23, 2007, pp. 9158-9161, published on web Aug. 1, 2007.*
International Preliminary Report on Patenability for corresponding PCT application PCT/US09/48250, Jan. 5, 2011. (Form PCT/IB/326/373/ISA/237).
International Search Report and Written Opinion for corresponding PCT application PCT/US09/48250, Sep. 23, 2009. (Form PCT/ISA220/210/237).

* cited by examiner

*Primary Examiner* — Brian Gulledge
*Assistant Examiner* — Isaac Shomer
(74) *Attorney, Agent, or Firm* — Timothy X. Gibson, Esq; Gibson & Dernier LLP (57) ABSTRACT

Nanoparticles are functionalized for use as bio-imaging probes using a novel, modular approach. Particle surface modification is based on a phosphonate monolayer platform on which was built a multi-segmented, multi-functional film: the first segment provided hydrolytic stability, the second aqueous suspendability, and the third, selectivity for cell attachment. In vitro imaging experiments visualized nanoparticle-cell surface binding. Peptide-derivatized nano-particles were not displaced from cells by soluble peptide. Methods for coating the host particles and use of rare earth ion-doped particles in imaging methods and photodynamic therapy methods are also disclosed.

31 Claims, 6 Drawing Sheets

MODULAR MONOLAYER COATINGS FOR SELECTIVE ATTACHMENT OF NANOPARTICLES TO BIOMOLECULES

CROSS-REFERENCE TO RELATED APPLICATION

The present application claims priority benefit under 35 U.S.C. §119(e) of U.S. Provisional Application Ser. No. 61/075,002 filed Jun. 23, 2008, the entirety of which is incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. CHE-0612572 awarded by the National Science Foundation.

FIELD OF THE INVENTION

In general the present invention relates to organophosphonate coated particles. Specifically, the present invention relates to modular monolayer coatings for selective attachment of nanoparticles to biomolecules and methods for making same.

BACKGROUND OF THE INVENTION

Effective bio-targeting luminescent nanoparticles must be non-toxic, small relative to the system they are imaging, stable over the course of the experiment, and able to target the desired entity. Semiconductor quantum dots have received considerable attention for biological applications such as cellular imaging, but have significant drawbacks, including constituent toxic elements (e.g., CdSe), need for UV excitation which can limit their use in vitro and compromise in vivo applications, difficulty to meet narrow particle size requirements, and requirement for extensive surface modification both to prevent ion loss and to bond appropriate bio-receptor molecules.

Untreated nanocrystals present drawbacks for use as biomolecular probes. Such particles tend to aggregate, and lack surface groups that can be used to attach biomolecular probes. While surface coating with silica/siloxane layers is a common method of enabling particle-biomolecule conjugation, this treatment can significantly increase particle size, which affects transport to and into cells, and silica and siloxane coatings can be hydrolytically unstable under physiological conditions.

Other nanoparticles such as rare earth ion-doped yttrium oxide ($Y_2O_3$) are attractive targeting agents for several significant reasons: they are benign in vitro and in vivo and can be made with diameters<20 nm. They can be synthesized to have strong emission in the UV, visible, or IR by varying lanthanide dopant ions (so narrow particle size distributions are not necessary), and can be doped for down- or up-conversion emission. Yet, rare earth ion-doped $Y_2O_3$ nanoparticles have seen only limited use for targeting biological systems. Techniques that would enable yttria nanoparticles to satisfy the requirements for targeting agents have heretofore been unattainable.

Hence, there exists a need for robust nanoparticles and methods of making same functionalized for bonding to biomolecules.

SUMMARY OF THE INVENTION

This need is met by the present invention. In accordance with one aspect of the present invention nanoparticles functionalized for bonding to biomolecules are provided which include modular, multi-functional phosphonate monolayers synthesized thereon. The inventive nanoparticles include tailored monolayers that are stable under physiological conditions, simultaneously protect the particle-phosphonate interface from hydrolysis and impart particle suspendability in aqueous media, and enable polyvalent bonding of targeting biomolecules to the particles. Nanoparticles such as $Y_2O_3$ can be functionalized to promote increased cell attachment through specific, peptide-cell surface receptor-mediated interactions. Using a high yielding, modular approach to $Y_2O_3$ particle surface modification, desired nanoparticle characteristics can be achieved: the first segment 11-hydroxyundecylphosphonate (PUL) protects the monolayer-particle interface from hydrolysis; the second fragment (tri[ethylene glycol]) imparts aqueous suspendability; and, the terminal section (bio-molecule) enables biological targeting. This method is effective for modulating cell-bulk particle interactions in vitro and should be readily amenable to modification and functionalization of luminescent nanoparticles for bio-imaging purposes.

In accordance with another embodiment luminescent, doped $Y_2O_3$ nanoparticles surface treated with a modular monolayer are provided which are selective for cell attachment in in vitro targeting applications. In vitro data suggest that unmodified nanoparticles such as $Y_2O_3$ can be problematic for non-specific cell binding; however, through appropriate surface modification as disclosed herein to give an oligo (ethylene glycol)-terminated surface, non-specific interactions can be reduced. In accordance with the present invention, doped or undoped $Y_2O_3$ nanoparticle surfaces can be easily and reproducibly functionalized in high yield via a modular scheme based on organophosphonate monolayers that enables control of nanoparticle surface properties. The nanoparticles can be made more cell adhesive or more cell resistant than the native ones by bonding an RGD-containing peptide or an oligoethylene glycol moiety, respectively. This modular scheme can be used to derivatize luminescent, $Eu^{3+}$-doped nanoparticles with an RGD peptide; in vitro experiments show that increased cell surface-nanoparticle binding interactions are achievable and not suppressed by added soluble peptide. The modular methods described herein may be expanded to examine peptide-receptor specificities; a small library of differently "colored" nanoparticles, each terminated with a different peptide sequence, can be used to identify peptide-ligand specific cell surface receptor sites U.S. Published Patent Application No. 2009/0028792, incorporated by reference herein in its entirety, relates in part to providing a phosphonate monolayer that may be functionalized for covalent bonding to a bio-molecular probe targeting reagent. The single layer coated particles and coating methods disclosed therein, including the nanoparticle synthesis methods and techniques for attaching bio-molecule targeting agents, can be applied to the presently-described particles having additional layers of modular coating agents. The products prepared according to the teachings of U.S. Published Patent Application No. 2009/0028792 can also be prepared using the presently-described coated particles, and the therapeutic, analytic and imaging uses described therein can also be performed without significant modification using the presently-described coated particles. Thus, nanoparticles made in accordance with the present methods can be used in imaging methods, in vivo and in vitro assays and photodynamic therapy cancer treatment methods employing rare earth ion-doped coated particles covalently bonded to biomolecular probe targeting ligands.

The inventive methods can be used to coat rare earth ion-doped luminescent particles. Such particles are doped prior to coating with ions of one or more rare earth elements. Examples of rare earth elements include europium, cerium, terbium, dysprosium, holmium, erbium, thulium, ytterbium and lutetium.

According to yet another aspect of the present invention particle-probe conjugates are provided, formed by the covalent attachment of biomolecular probes to functional groups on the organic moiety of the organophosphonate particle coating. Particle-probe combinations may be prepared, such as the combinations using rare earth ion-doped particles disclosed by Zarling et al., U.S. Pat. No. 5,698,397, the disclosure of which is incorporated by reference, with the present invention representing an improvement in the method by which the particle-probe combinations of the above-referenced patent are prepared.

Tissues can thus be imaged by conventional techniques by labeling the tissue to be imaged with the rare earth ion doped particle-probe conjugates of the present invention using a probe component that binds preferentially to biological markers on the tissue to be imaged. Visible light emission from the particles can be observed via conventional light microscopy or an image can be generated from either visible or infrared light emission from the particles using conventional imaging hardware and software.

Therefore, according to still yet another aspect of the present invention, a method is provided for tissue imaging by labeling a tissue to be imaged with the organophosphonate-coated rare earth ion-doped particles of the present invention covalently bonded to probes that bind specifically to biological markers on the tissue; exciting the particles with tissue-penetrating electromagnetic radiation of a wavelength that stimulates the rare earth ions to emit photons; and converting the photon emission to a visible image. Nanometer (nm) scale particles are preferred, with particles having a particle size capable of penetrating the blood-tissue barrier being more preferred. Tissue-penetrating radiation capable of stimulating rare-earth ions to emit photons includes infrared wavelengths. The emitted photons may include UV, visible and infrared wavelengths.

Depending upon location, the tissue can be imaged in-vivo via minimally invasive internal instrumentation, or by exposing the tissue to be imaged in a sterile environment to permit the image to be captured. The present invention can further be used to obtain high resolution images of ex-vivo tissue sections of biopsy samples. In addition, one of ordinary skill in the art will understand how the present invention can be applied to the analyte detection techniques of the above-referenced U.S. Pat. No. 5,698,397.

The rare earth ion-doped coated particle-probe conjugates can also be employed with photodynamic therapy (PDT) methods. PDT is a light based cancer treatment where a photosensitizing drug is activated with a visible light. PDT is executed by administering the photosensitizing drugs (which are non-toxic and inactive without light) intravenously and/or locally and illuminating them with visible light. The light energy is captured by the photosensitizing drugs, which then transfer that energy to produce toxic species, typically by transferring that energy to molecular oxygen, generating excited quantum states of oxygen that effect PDT. It is an extremely effective cancer treatment and works by several mechanisms: direct cell kill, induced cell death (apoptosis), destruction of neovascularization supplying a tumor, induction local inflammation response to tumor, systemic immune response to tumor. The greatest limitation to employing PDT is light delivery, as the activating wavelengths of visible light only penetrate tissue for several millimeters. Until now it was not possible to treat a tumor with PDT if it was not accessible for having a light shone directly on it.

Yet another aspect of the present invention thus provides a PDT method for treating a living being in need thereof using the particle-probe conjugates of the present invention. At least one photosensitizing agent is introduced into the body of the living being in proximity to diseased tissue, wherein the photosensitizing agent generates species toxic to the diseased tissue in response to stimulation by visible or infra red light. Rare earth ion-doped coated particle-probe conjugates of the present invention in which the probe binds specifically to the diseased tissue are introduced into the body of the living being, wherein the rare earth ions in the particles are excitable by tissue-penetrating radiation to produce visible or infra-red light and the photosensitizing agent is in sufficient proximity to the particle-probe conjugate to stimulate the production of the toxic species. Tissue-penetrating radiation for exciting the luminescent compound is then applied thereto from a source that is within minimally invasive or non-invasive excitation proximity of the luminescent compound.

The foregoing and other objects, features and advantages of the present invention are more readily apparent from the detailed description of the preferred embodiments set forth below, taken in conjunction with the accompanying drawings.

DETAILED DESCRIPTION OF PREFERRED EMBODIMENTS

In general a method of making a coated nanoparticle in accordance with the present invention includes coating a nanoparticle of interest with a suitable monolayer, treating the monolayer with a cross-coupling agent appropriate for binding a conjugate of a receptor of interest to the surface of the nanoparticle, and binding the conjugate. In one embodiment the present invention includes a method which provides modular, multi-functional phosphonate monolayers synthesized on a nanoparticle surface, such as but not limited to a $Y_2O_3$ nanoparticle surface, to satisfy criteria necessary for binding to a biomolecule. The tailored monolayers are stable under physiological conditions, simultaneously protect the particle-phosphonate interface from hydrolysis and impart particle suspendability in aqueous media, and enable polyvalent bonding of targeting biomolecules to the particles. Luminescent, doped nanoparticles, such as but not limited to europium-doped $Y_2O_3$ nanoparticles, surface treated with a modular monolayer are selective for cell attachment in in vitro targeting applications.

The present invention can be practiced with essentially any particle which may or may not be doped with a plurality of the same or different rare earth ions. Oxide particles have the formula MO when M has a valence of two, $M_2O_3$ when M has a valence of three, and so forth. Oxysulfide particles have the formula $M_3O_2S$ or $M_3OS_2$ when M has a valence of two, $M_2O_2S$ or $M_2OS_2$ when M has a valence of three, and so forth. M is preferably a lanthanide and more preferably is yttrium when the particle is an oxide or oxysulfide and lanthanum when the particle is a halide.

Particles can optionally be doped prior to coating with any rare earth element or combinations thereof (i.e., europium, cerium, terbium, dysprosium, holmium, erbium, thulium, ytterbium, lutetium, etc.) with europium, cerium, terbium, holmium, erbium, thulium and ytterbium being preferred, and the following combinations also being preferred: ytterbium and erbium, ytterbium and holmium and ytterbium and thulium. M can be, but is not limited to, lanthanum, yttrium, lead, zinc, cadmium, and any of the Group II metals such as, magnesium, calcium, barium, aluminum, and any mixtures thereof or a metalloid selected from silicon, germanium and II-IV semi-conductor compounds.

One type of luminescent particle host material generally has the structure $L_2O_3$, wherein L represents one or more rare earth elements of the lanthanide series. Luminescent materials suitable for use in the invention may contain a plurality of $L_2O_3$ compounds. Examples of suitable phosphor host materials include sodium yttrium fluoride ($NaYF_4$), yttrium oxide ($Y_2O_3$), lanthanum fluoride ($LaF_3$), lanthanum oxysulfide ($La_2O_2S$), yttrium oxysulfide ($Y_2O_2S$), yttrium fluoride ($YF_3$), gadolinium fluoride ($GdF_3$), barium yttrium fluoride ($BaYF_5$, $BaY_2F_8$), calcium tungstate ($CaWO_4$) and gadolinium oxysulfide ($Gd_2O_2S$).

Examples of rare earth ion-doped luminescent particles suitable for use in the present invention are described in U.S. patent application Ser. No. 11/494,157, the disclosure of which is incorporated by reference. Specific examples of luminescent materials include Yttrium Oxide:Terbium ($Y_2O_3$:Tb), Gadolinium Oxysulfide:Europium ($Gd_2O_2S$:Eu); Lanthanam Oxysulfide:Europium ($La_2O_2S$:Eu); and Gadolinium Oxysulfide:Promethium, Cerium, Fluorine. Other infra red excitable luminescent materials are disclosed in this application including rare earth ion-doped $Er_2O_3$ and $Y_2O_3$.

Two rare earth element ions may be paired as activator couples to tailor particle performance to specific absorption and emission wavelengths. For example ytterbium and erbium act as an activator couple in a phosphor host material such as barium-yttrium-fluoride. The ytterbium ions act as absorber, and transfers energy non-radiatively to excite the erbium ions. The emission is thus characteristic of the erbium ion's energy levels.

Suitable activator couples are selected from: ytterbium/erbium, ytterbium/thulium, and ytterbium/holmium. Other activator couples suitable for up-conversion may be used. By combination of the host materials with the activator couples, at least three phosphors with at least three different emission spectra (red, green, and blue visible light) are provided. Typically the absorber is ytterbium and the emitting center is selected from: erbium, holmium, terbium, and thulium; however, up-converting phosphors of the invention may contain other absorbers and/or emitters.

Examples of other suitable oxide, oxysulfide and halide phosphor particles and the methods by which they are made are described by Riman et al., U.S. Pat. No. 6,699,406, Kane, U.S. Pat. No. 5,891,361, Ohwaki et al., U.S. Pat. No. 5,541,012 and Austin et al., U.S. Patent Application Publication No. US-2006-0269483-A1. The disclosures of all three patents and the published application are incorporated herein by reference.

The particles can also be formed by a high temperature combustion synthesis technique, such as is disclosed by Ju et al., U.S. Patent Application Publication No. 2007-0069180-A1 and U.S. patent application Ser. No. 11/537,159, the disclosures of both of which are incorporated herein by reference. Other processes for forming exemplary luminescent materials include sol-gel processes; aerogel processes; xerogel processes; co-precipitation; solution processes; spray pyrolysis processes; spray flame pyrolysis processes; chemical vapor synthesis processes; emulsion liquid membrane methods; and hydrothermal processes. Such processes can also be use to form particles that are not doped with rare earth ions.

The particles are then coated with an organophosphonate self-assembled monolayer covalently bonded to the particle surface by suspending the particles in an organophosphonic acid solution in a solvent until self-assembled phosphonate-bonded monolayers of the organophosphonic acid attach covalently to the particle surfaces. A solvent in which the organophosphonic acid is soluble should be used. The choice of solvent will depend upon the organophosphonic acid selected, which will vary in hydrophilicity depending upon whether the objective of the coating is to make the particle more or less hydrophilic than the native particle surface. The polarity of the solvent selected will increase with organophosphonate hydrophilicity, and vice versa.

Polar solvents used in the preparation of hydrophilic organophosphonic acid solutions include water, methanol, ethanol, isopropanol, n-propanol, n-butanol, hexanol, ethylene glycol, ethyl acetate, tetrahydrofuran (THF) and combinations thereof. Non-polar solvents used in the preparation of hydrophobic organophosphonic acid solutions include carbon tetrachloride, methylene chloride, toluene, chloroform, and combinations thereof. Both hydrophilic and hydrophobic organophosphonic acids are soluble in certain solvents such as ethyl acetate, THF, ethanol, methanol, and combinations thereof. Solution concentrations range between about 0.1 vol. % and about 80 vol. %, and preferably between about 1 vol. % and about 50 vol. %.

The particles are suspended in the organophosphonic acid solution by conventional means, such as physical stirring or sonication. Between about 0.1 and about 90 wt. % of particles, and preferably between about 0.1 and about 5 wt. %, are added to the organophosphonate solution. The suspension step is performed for at least 0.5 hours and preferably between about two and about 24 hours. The reaction proceeds under ambient conditions; however temperatures between about 0° C. and the boiling point of the solvent can be used.

Some oxide particles, such as yttrium oxide, form carbonates under ambient conditions that are preferably removed by pre-treatment of the particles with trifluoracetic acid alone or diluted to between about 0.1 and about 25 vol. % with a solvent such as, for example, acetonitrile. The particles are then washed with deionized water prior to suspension in the organophosphonic acid solution.

When the particles are oxides or oxysulfides, the organophosphonic acid has the formula $R-P(=O)(-OH)_2$, wherein R is an organic moiety that is either more or less hydrophilic than the native particle surface, and is optionally functionalized either to make the R group more or less hydrophilic, or for conjugation of biomolecular probe targeting reagents.

R is selected from linear or branched alkyl or alkylenyl moieties with from about two to about 40 carbon atoms and 0 to about 20 heteroatoms preferably selected independently from oxygen and nitrogen. Preferred alkyl and alkylenyl moieties are linear or branched and have from about two to about 20 carbon atoms and 0 to about ten heteroatoms preferably selected independently from oxygen and nitrogen.

Hydrophobic R groups are used to form a coating less hydrophilic than the native particle surface, while hydrophilic R groups are used to form a coating more hydrophilic than the native particle surface. When R is a hydrophobic group, for example an alkyl or alkylenyl with about two to about 40 carbon atoms and less than about four oxygen or nitrogen atoms, the coated particle is more hydrophobic than the native particle surface. Examples of hydrophobic R groups include butyl, hexyl, octyl, dodecyl, octadecyl and undecyl groups, and the like.

When R is a hydrophilic group, for example, a saturated or unsaturated alkyl or alkylenyl groups with about two to about 40 carbon atoms and either one or more hydrogen bonding functional groups or from about three to about 20 heteroatoms preferably selected from oxygen or nitrogen atoms, the coated particle is more hydrophilic than the native particle surface. Examples of hydrophilic R groups include R groups substituted with one or more hydrogen bonding functional groups including polyols or sugars, carboxyls, carboxylates, amines, hydroxyls, alkoxys, and tetraorganoammonium groups, and R groups that are poly(alkylene oxide) moieties, among which polyethylene glycols are preferred and tetraethylene glycols are even more preferred.

Also preferred are organic moiety R groups that are disposed to participate in a close-packing arrangement when the acid is adsorbed onto the particle surface.

The R groups may be optionally substituted with one or more functional groups selected from hydroxyl functional groups, amino functional groups, carboxylic acid functional groups, carboxylate functional groups, phosphonic acid functional groups, phosphonate functional groups, ether functional groups, polyether functional groups and thiol functional groups. The use and selection of functional groups will depend up on the extent to which the coating is intended to increase or decrease particle hydrophilicity, which can be readily determined by one of ordinary skill in the art without undue experimentation.

The functional group substituents may be selected for covalent attachment of biomolecular probe targeting reagents to rare earth ion-doped particles, in which case the functional group for biomolecular probe covalent attachment is preferably omega-substituted on the organophosphonic acid R group. When R is a poly(alkylene oxide), the omega-substituent is an ether or a hydroxyl group, which may be activated by conventional methods to conjugate a probe molecule.

After the particles are coated, the suspended particles are separated from the organophosphonic acid solution by centrifuging according to conventional means. A polar solvent such as methanol may be added to help precipitate the particles on centrifugation, after which the supernatant solvents are decanted and the particles recovered for subsequent washing. The particles are washed by manual shaking in methanol to which a weak solution of NaOH (0.01 to 0.1 M) in methanol has been added. The particles are collected again by centrifugation and dried.

The reaction yields particles coated with organophosphonic acid self-assembled monolayers covalently bonded to the particle surface. The particles may be used as-is for essentially any end use for a micron- or nano-sized particle that would benefit from modification of the hydrophilicity of the native surface of the particle. Examples of such end-uses include essentially any end-use in which a hydrophilic or hydrophobic product is needed for a stable dispersion or suspension in a particular solvent to be formed, or to encapsulate stably in a micelle, cyclodextrin or liposome, so that particles do not float to the top of or settle to the bottom of bulk quantities of the solvent for the dispersion or suspension, or so that the particle is not ejected from the micelle, cyclodextrin or liposome.

Micelle, cyclodextrin and liposome-encapsulation processes are essentially conventional. Particles with coatings more hydrophobic than the native particle surface may be encapsulated by a micelle capable of suspending a hydrophobic particle in a hydrophilic medium. Such particles may also be encapsulated by a cyclodextrin or liposome with a hydrophobic core and a hydrophilic exterior for suspension in a hydrophilic medium. Particles with coatings less hydrophobic than the native particle surface may be encapsulated by a micelle capable of suspending a hydrophilic particle in a hydrophobic medium. Such particles may also be encapsulated by a cyclodextrin or liposome with a hydrophilic core and a hydrophobic exterior for suspension in a hydrophobic medium.

The organophosphonic acid coated rare earth ion-doped particles of the invention with omega-functionalized organic moieties can be attached to one or more probe(s) that bind specifically to biological markers in tissues to serve as a reporter (i.e., a label or detectable marker) of the location of the probe(s). The coated up-converting particles can be attached to various probes, such as anti-bodies, streptavidin, protein A, polypeptide ligands of cellular receptors, polynucleotide probes, drugs, antigens, toxins, and others. Attachment of the coated particle label to the probe can be accomplished using various linkage chemistries, depending upon the nature of the specific probe, and made possible by the omega-functionalized organic moieties on the organophosphonic acid coatings on the particle surfaces.

A preferred attachment method adapts the method described by Tanke et al., U.S. Pat. No. 5,043,265, the disclosure of which is incorporated by reference. Heterobifunctional cross-linkers are employed that can be made to link a biomolecular probe to coated particles in three steps: (1) bind the cross-linker to the omega-functionalized organophosphonate coating on the phosphor, (2) separate the unbound cross-linker from the coated particles, and (3) bind the biomolecular probe to the washed, linked coated particle. This method prevents undesirable cross-linking interactions between biomolecular probes and reduces irreversible aggregation as described by the Tanke et al. patent. Examples of suitable heterobifunctional cross-linkers, omega-functionalities, and linkable biomolecular probes include, but are not limited to:

| Coating Functionality | Biomolecular Crosslinker | Heterobifunctional Probe |
|---|---|---|
| carboxylate | N-hydroxysuccimide 1-ethyl-3-(3-dimethyl-amino-propyl)carbodiimide (EDCI) | Proteins (e.g., Ab, avidin) |
| primary amine | N-5-azido-2-nitrobenzoyl oxysuccimide (ANB-NOS) N-succinimidyl (4-iodoacetyl) aminobenzoate (SIAB) | All having 1° amine |
| thiol(reduced sulfonate) | N-succinimidyl (4-iodoacetyl) aminobenzoate (SIAB) | Proteins |

Suitable cross-coupling agents are readily available to one having skill in the art. References are available such as the Pierce catalog, accessible at www.piercenet.com, which includes an on-line cross linker selection guide enabling a user to select an appropriate agent for a particular purpose.

One embodiment of the present invention provides organophosphonate-coated particles in which the organic moiety of the organophosphonate is a poly(alkylene oxide), such as tetra-ethylene glycol. Bifunctional poly(alkylene oxide) hydrazides and dihydrazides for linking two compounds having free carboxylic acid groups and methods of attachment are disclosed in Kohn et al., U.S. Pat. App. Publication No. 2005-0118227-A1, the disclosure of which is incorporated herein by reference. The method disclosed therein can be readily adapted to conjugate organophosphonates with poly(alkylene oxide) organic moieties to biomolecular probes with free carboxylic acid groups.

Otherwise the conjugation of poly(alkylene oxides) to biologically relevant peptides and polypeptides is routine and disclosed in Davis et al., U.S. Pat. No. 4,179,377, the disclosure of which is incorporated by reference. Zalipsky et al., U.S. Pat. No. 5,455,027 discusses prior art subsequent to Davis et al. on this subject. The disclosure of Zalipsky et al. and the relevant prior art cited therein is incorporated herein by reference. The art of conjugating poly(alkylene oxides) to peptides, polypeptides and other relevant active molecules is well known and referred to as PEGylation. Techniques known to those of ordinary skill in the PEGylation art can be used to conjugate organophosphonates with poly(alkylene oxide) organic moieties to biomolecular probes with free carboxylic acid groups.

One requirement of PEGylation is that for the reactive moiety on the active molecule to be considered available for conjugation it must not contribute to the molecular activity so that PEGylation does not inactivate the active molecule. Likewise the poly(alkylene oxide)-phosphonate coated particles of the present invention must not be conjugated to sites on bio-molecular probes that would prevent binding of the probes to the probe target. Methods by which such sites may be protected from conjugation and the conjugation directed to an inert site are well known to those of ordinary skill in the art of PEGylation.

Omega-hydroxyl organophosphonate coatings, including coatings in which the organic moiety is a poly(alkylene oxide) can also be derivatized or activated with an acid chloride or chloroformate, $R_3$—C(=O)—Cl or $R_3$—O—C(=O)—Cl, respectively. The $R_3$ group can be a linear or branched alkyl or alkylenyl group, or an aryl or alkylaryl group. The $R_3$ group can be omega functionalized like the organic moiety or ring substituted with one of the above listed functional groups other than a hydroxyl group to replace the omega-hydroxyl group with a different omega-functionality. One of ordinary skill in the art will recognize other functional groups capable of reacting with acid chlorides and chloroformates in this manner.

Other methods by which carboxylic acid functionalized polymers are conjugated to functional groups of active molecules are described in the above-referenced Zalipsky et al. patent. Detailed chemical procedures for the attachment of various drugs and ligands to polymer bound free carboxylic acid groups have otherwise been described in the literature. See, for example, U.S. Pat. Nos. 5,219,564 and 5,660,822; Nathan et al, Bio. Cong. Chem., 4, 54-62 (1993) and Nathan, Macromol., 25, 44-76 (1992). The disclosures of both patents and both journal articles are incorporated herein by reference. These publications disclose procedures by which polymers having pendent free carboxylic acid group are reacted with moieties having reactive functional groups, or that are derivatized to contain active functional groups to form a polymer conjugate. The methods disclosed therein can also be readily adapted to conjugate organophosphonates with poly(alkylene oxide) organic moieties to biomolecular probes with free carboxylic acid groups.

Yttria nanoparticles do not suspend in aqueous media. Wettability of such nanoparticles can be controlled by attaching monolayers of simple phosphonic acids, which are stable in organic or aqueous media and about 1 nm thick. However, simple phosphonate treated nanoparticles adequate to satisfy the requirements for targeting agents have heretofore been unattainable. $Y_2O_3$ nanoparticles coated with a mixed aliphatic-hydrophilic "hybrid" monolayer, tetra(ethylene glycol)propylphosphonate (1a), are described by Traina et al., Langmuir, 23, 9158-9161 (2007), incorporated herein by reference in its entirety. Although such coated nanoparticles are stable in water at neutral pH, desorption occurs rapidly at physiological pH (7.5). It is believed that hydrolysis of the phosphonate-$Y_2O_3$ interface occurred because the 3-carbon alkyl chain was insufficiently hydrophobic to prevent water penetration to the interface.

$Y_2O_3$ nanoparticles prepared with a tetra(ethylene glycol) undecyl-phosphonate monolayer, 1b, were more stable than 1a at pH 7.5, but degradation of 1b still occurred. Moreover, synthesis of such "hybrid" precursors is tedious.

Synthesis of 1a and 1b.

n = 1, 1a
n = 9, 1b

A modular approach solving these problems is provided herein. The first module protects the particle-monolayer interface from hydrolysis, the second facilitates aqueous suspension, and the third serves to bond bio-molecule targeting agents. One skilled in the art will recognize any monolayer suitable for the particular application may be selected for the first module. Criteria for the first module should include resistance to hydrolysis for the particle-monolayer interface, however, the degree of resistance needed for a particular application may be considered against other factors. Likewise, while the second module should facilitate aqueous suspension, the particular compound employed can be tailored for a particular purpose. The third module is selected for its ability to bond the desired biomolecule targeting agent.

Experiments

Figure 1:
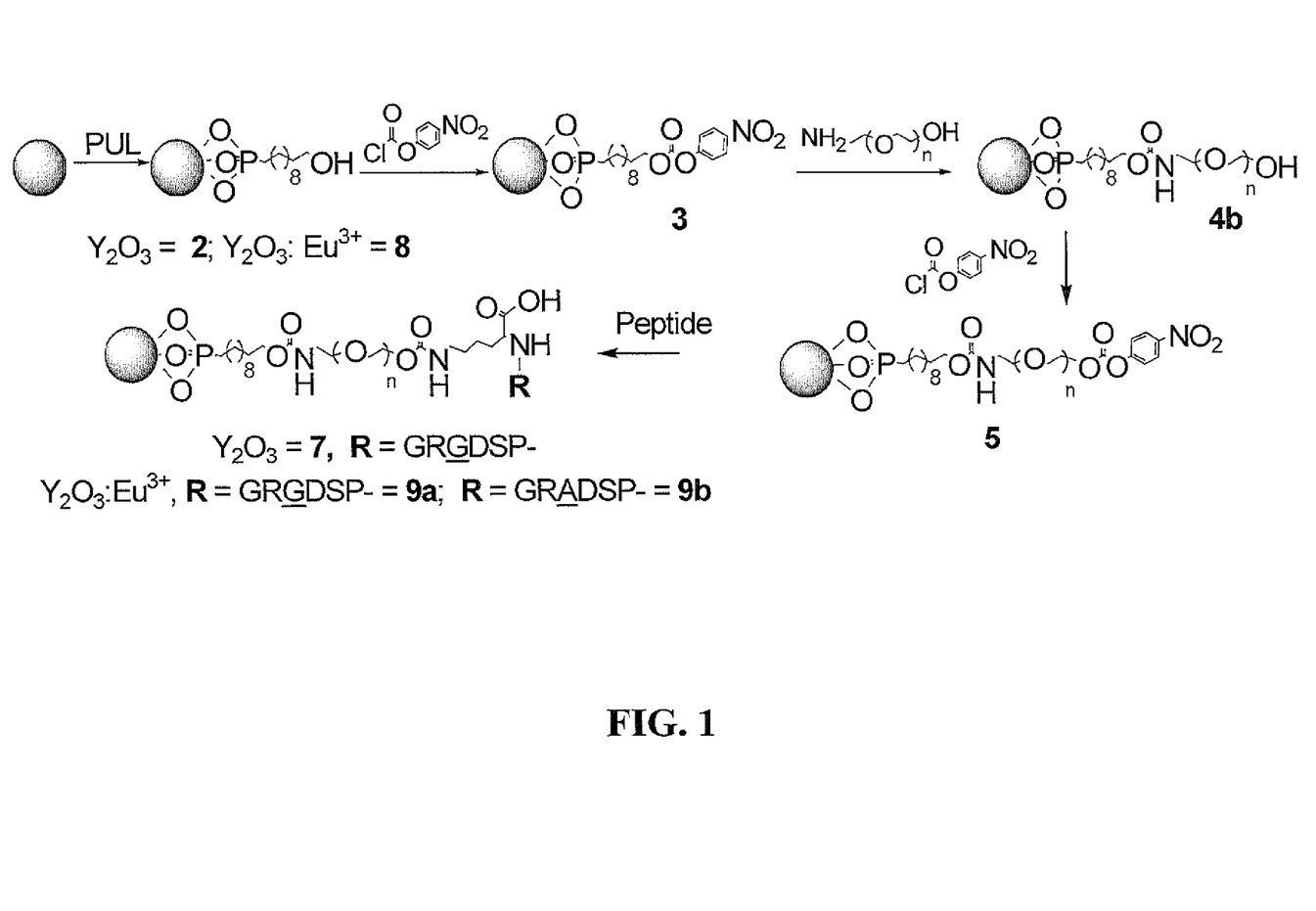
FIG. 1 depicts a modular approach to surface modification in accordance with one aspect of the present invention.
Figure 2:
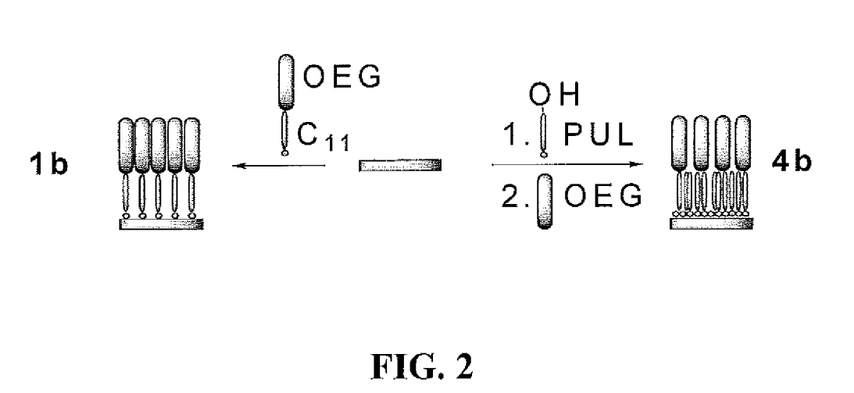
FIG. 2 depicts a comparison of chain packing of 1b and 4b.
Figure 3:
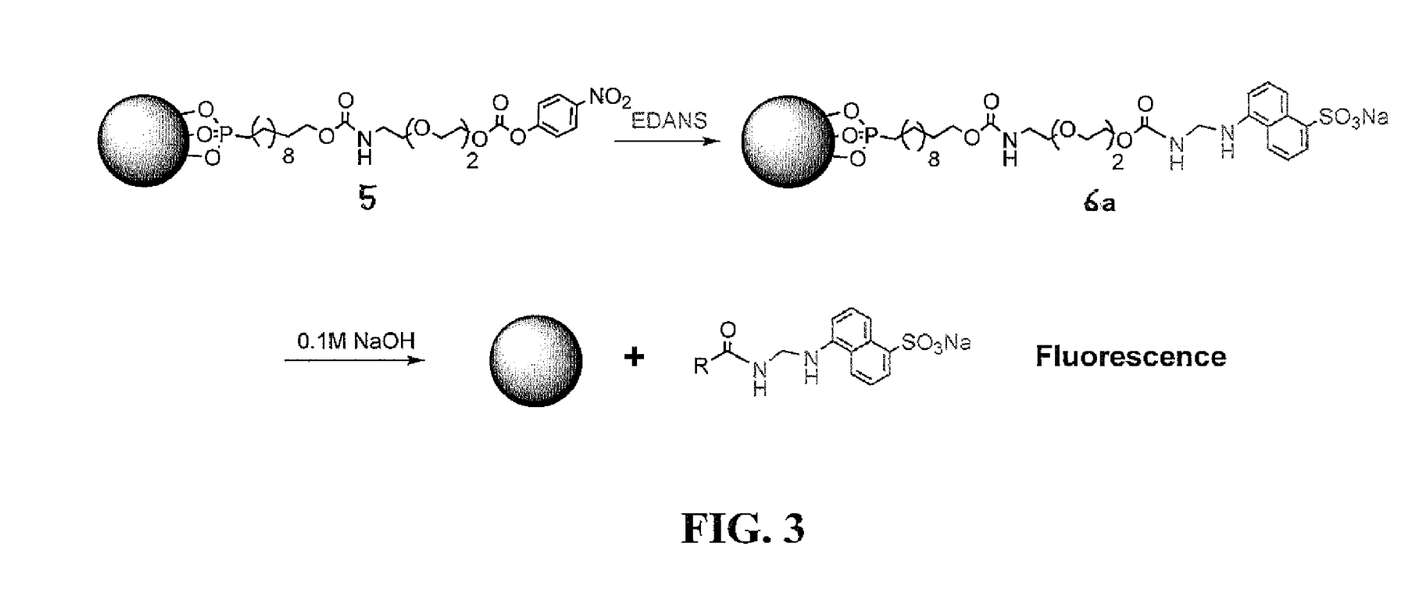
FIG. 3 is a depiction of a fluorescence-based procedure for determination of surface loading in accordance with the present invention.
Figure 4:
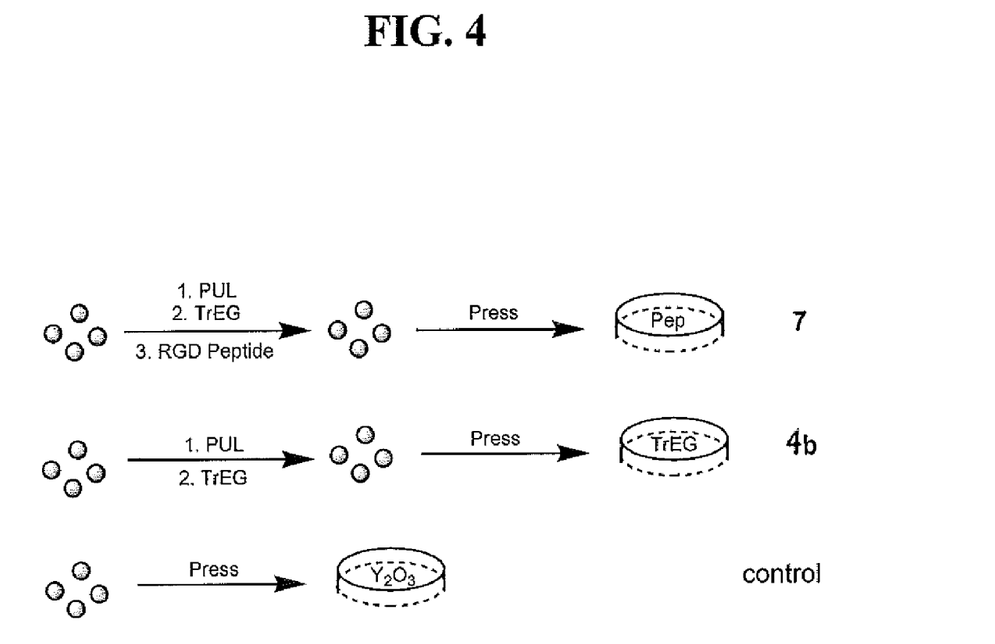
FIG. 4 is a schematic depiction of an in vitro experiment in accordance with the present invention.
Figure 5:
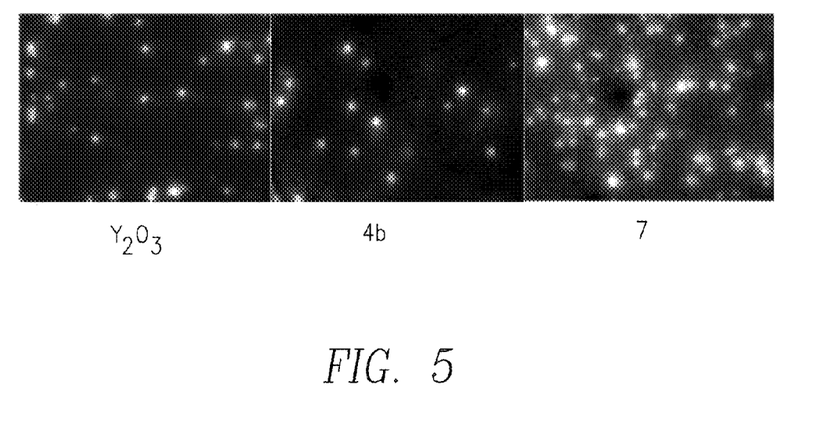
FIGS. 5 and 5A depict cell adhesion images (FIG. 5) and cell count data in accordance with the experiment depicted in FIG. 4.
Figure 5A:
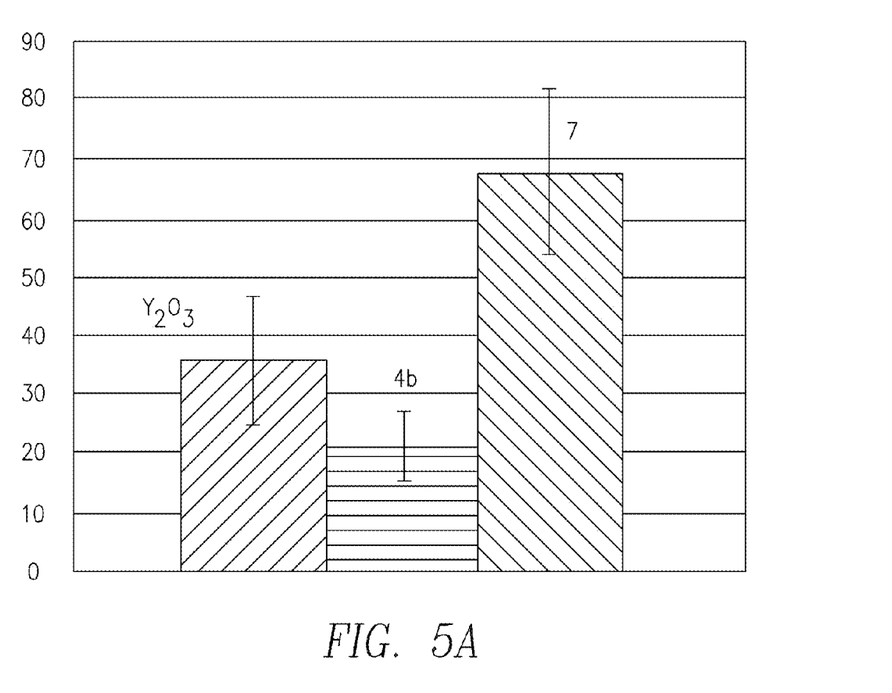
Figure 6A:
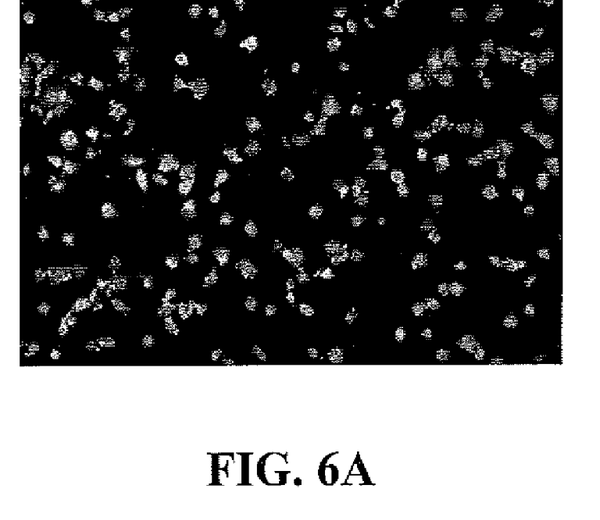
FIGS. 6A and 6B are micrographical depictions of non-specific adsorption/aggregation of RGD-modified nanoparticles 9b (FIG. 6A) versus adherence of cells by RAD-modified nanoparticles 9a (FIG. 6B) in non-confluent cell layers.
Figure 6B:
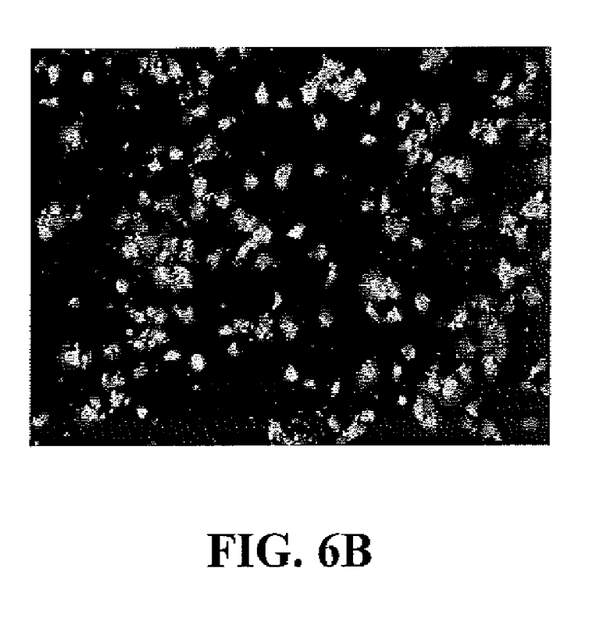

Now referring to FIG. 1, monolayers of 11-hydroxyundecylphosphonate (PUL) on $Y_2O_3$ nanoparticles (2) are stable at pH 7.5 for >12 days; thus PUL was chosen as the first module. Terminal —OH groups of PUL monolayers on metallic surfaces can be coupled with bio-molecules using activated ester reagents. p-nitrophenyl chloroformate reacts readily with $Y_2O_3$ nanoparticles 2 to give p-nitrophenyl carbonate derivatized particles (3, $v_{C=O}$=1768 $cm^{-1}$) that react with amines; p-nitrophenyl carbonate derivatized particles 3 reacted with hexylamine to give surface urethane ($v_{C=O}$=1700 $cm^{-1}$). The second module is thus introduced: tri(ethylene glycol) monoamine is bound to p-nitrophenyl carbonate derivatized particles 3 to give 4b, which has better aqueous suspendability than 2. Importantly, 4b is stable to hydrolysis at physiological pH. 1b and 4b are different in their hydrolytic stability despite similar molecular structures and aqueous wettability. As shown in FIG. 2, which shows the different chain packing of 1b and 4b, the monolayer constituents of 1b appear to pack less tightly on the surface because of the ethyleneoxy tail groups, allowing water penetration to the interface. In contrast, PUL can form a dense film on $Y_2O_3$ and thus be more water resistant; because of relative sizes of the alkyl and oligoethylene glycol units, the reaction of 3 with tri(ethylene glycol) monoamine would likely occur <100%. This difference in chain packing is believed to affect particle aqueous suspendability and film hydrolytic stability.

Referring to FIG. 1, treating 4b with p-nitrophenyl chloroformate gave 5 ($v_{C=O}$=1768; 1700 $cm^{-1}$), which can then bond the desired bio-targeting molecule via reaction with a primary amino group, discussed in further detail hereinbelow. For convenience in optimizing the third module, micron-sized $Y_2O_3$ particles (Aldrich) were used.

Now referring to FIG. 3, fluorescent dye sodium 5-([2-aminoethyl]amino)naphthalene-1-sulfonate (EDANS) was attached to 5 to give 6a; by cleaving the dye from the nanoparticles, surface bonding could be quantified via fluorescence measurements of supernatant concentrations, particle mass and surface area. Specifically, the EDANS concentration was quantified with reference to a linear plot of fluorescence intensity versus EDANS concentration that was generated from standard solutions of the dye. The concentration of EDANS and total volume of the supernatant were then used to obtain the amount of dye in solution, which corresponds to the amount of dye attached to the particle surface. The EDANS surface loading density was then calculated from the amount of surface-attached EDANS and the mass and surface area of the particles. In this way, the surface loading of dye on 6a was calculated to be 0.25±0.01 $nmol/cm^2$, which is similar to peptide loadings on PUL monolayers on $TiO_2$/Ti; this loading is assumed to be comparable for attachment of biomolecules of similar "footprint" to that of EDANS. The aforementioned coupling procedure is expected to be readily compatible with attachment of larger biomolecules, such as proteins and peptides that are relevant to biological targeting.

In vitro and in vivo imaging applications require $Y_2O_3$ nanoparticles that are modified with targeting moieties; these particles must be bio-compatible in that they should be free from non-specific cell-nanoparticle interactions that could compromise diagnostics. To determine bio-compatibility and cell-particle interactions, simple fibroblast adhesion studies were conducted on pellets pressed from derivatized $Y_2O_3$ powders. Now referring to FIG. 4, three different systems were examined: untreated $Y_2O_3$ (control); tri(ethylene glycol)-terminated $Y_2O_3$ (4b); and RGD-functionalized $Y_2O_3$ (7). Pellets were introduced individually into cell culture, and the cells were allowed to attach to them for 90 minutes. Non-adherent cells were removed by rinsing, the surfaces were visualized, and the number of adherent cells was quantified. Cell attachment on the $Y_2O_3$ control was modest, and the number of cells adhered to tri(ethylene glycol)-derivatized surface 4b was reduced by 42% versus the control surface. Conversely, pellet 7, which was conjugated to a known cell-attractive peptide (see, Pierschbacher et al., Cell Attachment Activity of Fibronectin Can Be Duplicated by Small Synthetic Fragments of the Molecule. *Nature* 1984, 309, 30-33) showed greatly enhanced cell adhesion over the $Y_2O_3$ control (1.9×) (on left in FIGS. 5 and 5A) and 4b (3.3×) (middle in FIGS. 5 and 5A). Pellet 7 information is depicted in the right hand photo of FIG. 5 and on the right in FIG. 5A.

Now referring to FIG. 2, luminescent $Eu^3$-doped (5%) $Y_2O_3$ nanoparticles 8 were synthesized by precipitation of $Y(OH)CO_3$ particles from a refluxing, aqueous solution of $Y^{3+}$ and $Eu^{3+}$ salts and urea; calcining at 785° C. for 1 hr gave cubic $Y_2O_3$:$Eu^{3+}$ (by powder X-ray diffraction). Adjustment of reagent concentrations gave particles with diameters ranging from ~40 nm to 80-120 nm (by TEM). The latter sizes were used for subsequent experimentation; this diameter range is a compromise between the small sizes necessary for biological transport and the processing ease of larger particles. The emission spectrum had a strong band at 612 nm with less intense peaks at 591 and 630 nm, consistent with reported work on luminescent $Eu^{3+}$-doped $Y_2O_3$ nanoparticles. Importantly, these nanoparticles were easily visualized using a standard fluorescence microscope under UV (~365 nm) or blue (~488 nm) excitation; therefore, these particles were deemed suitable for detection in biological imaging experiments.

It is noted the same modular methods employed with respect to undoped nanoparticles described hereinabove are used for the doped nanoparticles. Some aggregation of the luminescent nanoparticles 8 was observed, so they were sonicated in THF prior to and during PUL monolayer deposition. The nanoparticles were then derivatized with tetraethylene glycol monoamine and then GRGDSPK to give 9a. Control 9b used cell adhesion-inactive G$\overline{RA}$DSPK. Suspensions of 9a and 9b were introduced separately into fibroblast cell culture ($10^5$ cells/ml; cells were prestained with cell-tracker dye) and were allowed to attach for 3 h; the cells were then washed to remove unbound particles, fixed, and visualized by fluorescence microscopy. Only the doped nanoparticles were visible under UV (365 nm) illumination, but blue (488 nm) irradiation excited both dye-stained cells and nanoparticles. Images of cells treated with control 9b showed only some large particle aggregates but no specific particle binding to the cells. In contrast, 9a showed cell attachment and little aggregation. Nanoparticle-cell binding was distinguished from simple precipitation using a non-confluent cell layer (~50% substrate coverage) that was treated with 9a or 9b. Most of the cells treated with 9a were covered with nanoparticles but very little 9a deposited on the substrate between the cells; few cells exposed to 9b were bound to particles (FIGS. 6A and 6B). Cell binding by 9a was not inhibited by soluble GRGDSPK. RGD-integrin binding is reversible; but due to their size, particles of 9a cannot be resuspended after cell interaction, which inhibits displacement by the soluble peptide. Importantly for cellular targeting, nanoparticles of 9a may act as polyvalent binding species, which would greatly enhance cell binding of the bio-conjugated particles vs. the soluble peptide: based on calculated EDANS surface loadings, and assuming an average particle diameter ≈100 nm, each nanoparticle can have >$10^4$ surface-attached peptide molecules on it, thus making it possible for the particle to bind simultaneously to several receptor sites on the cell surface.

The foregoing in vitro imaging experiments demonstrate the effectiveness of a modular approach to surface functionalization for the preparation of nanoparticle bio-imaging probes. This coating method simultaneously enables the nanoparticles to be suspended in aqueous, physiological media; protects the monolayer-particle interface from hydrolysis; and, provides imaging specificity through a biotargeting molecule. Thus it satisfies all conditions necessary for a successful imaging agent: size (~3 nm); specificity; and stability. With choice of the correct terminal targeting moiety, the presently disclosed nanoparticle conjugation methods make possible imaging of a variety of biological systems.

The particle-probe conjugates of the present invention are useful for medical diagnostic imaging. In one embodiment, particles coupled to probes that bind to biological markers are made to emit visible or IR radiation when excited with visible (red) or IR radiation, so that a patient can be irradiated with visible or IR radiation after the particle-probe conjugate is administered systemically or locally, and tissues with the biological marker to which the particles bind are detected with IR or visible light detection equipment.

Imaging methods with which the rare earth ion-doped probe-particle conjugates of the present invention may be used are disclosed in the above-referenced Austin et al., U.S. Patent Application Publication No. US-2006-0269483 and in PCT/US07/71717 filed Jun. 21, 2007, the disclosures of which is incorporated herein by reference. The Austin et al. publication also discloses methods by which the plurality of wavelengths within the spectrum emitted by a particle can be used to assay two or more properties of tissue to which the probe binds with a single excitation wavelength.

The rare earth ion-doped probe-particle combinations of the present invention can be substituted for and are intended to replace the probe-particle combinations disclosed in these patent applications. The probe-particle combinations of the present invention can be substituted for and are intended to replace essentially any prior art probe-reporter combination, regardless of whether the reporter is organic or inorganic, and regardless of whether the probe-reporter combination is used for imaging or to assay an analyte in vivo or in vitro. Probe-reporter uses include, but are not limited to, all uses of the probe-reporter combinations disclosed by, discussed as background art in and of record in the Austin et al. publication and in PCT/US07/71717, all of which are incorporated herein by reference, and all uses of the probe-reporter combinations disclosed by, of record in and discussed as background art in the above-referenced Tanke et al., U.S. Pat. No. 5,043,265 and Zarling et al., U.S. Pat. No. 5,698,397, as well as all probe-reporter uses disclosed by, of record in and discussed as background art in all patents and applications from which Zarling et al. claim priority, all patents and pending applications claiming priority to Zarling et al., and all patents and applications otherwise related to Zarling et al. All of the above-referenced patents and applications are incorporated herein by reference.

The rare earth ion-doped probe-particle combinations of the present invention are also useful in photodynamic therapy (PDT) treatment methods in which a compound or particle that upon excitation by tissue-penetrating wavelengths emits wavelengths that stimulate a photosensitizer compound co-administered therewith to produce a toxin for treatment of diseased tissue to which the probe-particle combination is targeted and binds. Such methods are described in the above-referenced PCT/US07/71717. The rare earth ion-doped probe-particle combinations of the present invention can be substituted for and are intended to replace the probe-particle combinations disclosed as useful for photodynamic therapy in the PCT/US07/71717. The rare earth ion-doped probe-particle combinations of the present invention can also be substituted for and are intended to replace the probe-reporter combination disclosed as being useful for PDT in the above-referenced Zarling et al. patents and applications.

In imaging, in vivo assaying and photodynamic therapy embodiments requiring injection, the particles are rare earth ion-doped, preferably monodisperse, and less than 150 nm in size to preclude capillary obstruction. The particles are more preferably monodisperse and less than 100 nm in size, and even more preferably of a monodisperse size capable of passing the blood-tissue barrier. In other delivery embodiments where the luminescent material is applied, for example by aerosolization or direct application to the chest cavity, larger particles can be used. Particle size is measured by Dynamic Light Scattering (DLS).

Imaging, in vivo assaying and photodynamic therapy compositions containing the rare earth ion-doped particle-probe combinations of the present invention, which may optionally include a photo-sensitizer dye in photodynamic therapy products, may be presented in forms permitting administration by the most suitable route. The invention also relates to administering such compositions to a patient in need thereof. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of solutions or suspensions than can be injected or administered to a treatment site following exposure of the treatment site via surgical means, for example.

The choice of vehicle and the rare earth ion-doped particle-probe combination in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used.

For parenteral administration, emulsions, suspensions or solutions of the particle-probe combinations in vegetable oil, for example sesame oil, groundnut oil or olive oil, or aqueous-organic solutions such as water and propylene glycol, injectable organic esters such as ethyl oleate, as well as sterile aqueous solutions of the particle-probe combinations, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Dispersion can also be prepared in glycerol, liquid polyethylene glycols, and mixtures thereof and in oils.

Sterile injectable solutions are prepared by incorporating the particle-probe combinations, with an optional amount of a photosensitizer dye for PDT compositions, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

Compositions for photodynamic therapy may also be prepared using the coated particles of the present invention without a probe covalently bonded thereto for methods in which the luminescent compound is applied directly to the diseased tissue without using a biomolecular probe targeting ligand. The coatings improve the stability of the particles within the formulation to be administered.

Although the present invention has been described in some detail by way of illustration for purposes of clarity of understanding, it will be apparent that certain changes and modifications may be practiced within the scope of the claims. The broad scope of this invention is best understood with reference to the following examples, which are not intended to limit the invention in any manner.

EXAMPLES

General Information. Tetrahydrofuran (THF, ACS grade, EMD) was distilled from Na/benzophenone before use. Acetonitrile (HPLC grade, EMD) was distilled from $CaH_2$ prior to use. Methanol and ethyl acetate (EMD) were used as received. Urea, europium(III) chloride hexahydrate, yttrium (III) chloride hexahydrate, hexylamine, p-nitrophenyl chloroformate, sodium hydroxide, yttrium oxide, DL-lysine, 11-bromo-1-undecene, acetyl chloride, trimethylsilyl bromide (TMS-bromide), dimethyl phosphite, tert-butyl peroxide (Aldrich), tetraethylene glycol (Alfa Aesar), triethylene glycol monoamine and tetraethyelene glycol monoamine (Molecular Bioscience) were used without further purification. N,N-Diisopropylethylamine (DIPEA, Aldrich) and methylene chloride (EMD) were dried over 4 Å molecular sieves prior to use. 5-([2-Aminoethyl]amino)naphthalene-1-sulfonic acid sodium salt (EDANS, Alfa Aesar) was used as received. Gly-Arg-Gly-Asp-Ser-Pro-Lys (GRGDSPK) peptide and Gly-Arg-Ala-Asp-Ser-Pro-Lys (GRADSPK) peptide (>98%, American Peptide Company) were used as received. 11-Hydroxyundecylphosphonic acid (PUL) was synthesized according to the procedure disclosed in Putvinski et al., Self-Assembly of Organic Multilayers with Polar Order Using Zirconium Phosphate Bonding between Layers. *Langmuir* 1990, 6, 1567-1571, incorporated in its entirety herein by reference. IR spectra were recorded using a Smart Orbit diamond attenuated total reflectance (ATR) attachment on a Nicolet 6700 FT-IR spectrometer. Fluorescence measurements were made using a Perkin Elmer LS 50 fluorescence spectrometer. Luminescence spectra of synthesized nanoparticles were obtained by dispersing nanoparticles onto a glass slide fitted with double-sided tape. TEM images were captured using a Zeiss 910 TEM and powder X-ray diffraction patterns were recorded on a Rigaku MiniFlex X-Ray Diffractometer.

Example 1

Phosphonate film deposition on $Y_2O_3$. Yttrium oxide powder (~1 g) was dispersed by sonication in 60 ml THF in a 250 ml round-bottom flask. A solution of phosphonic acid (PUL, 12 mg, $4.76\times10^{-5}$ mol, in 25 ml THF) was added to the powder suspension, and the reaction mixture was stirred for 3 hrs at room temperature. The powder was then collected by centrifugation and subsequently washed to remove excess phosphonic acid. The washing procedure was performed by dispersing the powder in 80 ml methanol containing 0.65 ml 0.05M NaOH/methanol solution and shaking this suspension for 6 min. The particles were then collected by centrifugation and the washing procedure was performed again. The powder was then washed a third time in a similar way but with a solution of 60 ml methanol, 20 ml deionized water, and 0.3 ml 0.05 M aqueous NaOH. The powder was subsequently dried in vacuo to yield $Y_2O_3$.

Example 2

Reaction of 5 with Hexylamine (6a) or Triethylene Glycol Monoamine (6b)

$Y_2O_3$ powder terminated with p-nitrophenyl carbonate (5) was put into a 100 ml round-bottom flask equipped with an argon inlet and stir bar. Dry THF (60 ml) was added, and the suspension was stirred under argon for 5 min. Diisopropylethylamine (0.75 ml, $4.31\times10^{-3}$ mol) and a solution of either hexylamine (20 mg, $1.98\times10^{-4}$ mol) or triethylene glycol monoamine (35 mg, $2.34\times10^{-4}$ mol) in dry THF was added, and the reaction mixture was stirred under argon for 20 hrs. The powder was then collected by centrifugation. Excess reagents were removed by dispersing the powder in 80 ml methanol and 0.05 M NaOH/methanol (0.65 ml) and manually shaking this suspension for 6 min. The powder was recovered by centrifugation. This washing procedure was performed twice to yield 6a (hexylamine conjugate) or 6b (triethylene glycol monoamine conjugate).

Example 3

Reaction of 7 with 5-([2-aminoethyl]amino)naphthalene-1-sulfonic Acid Sodium Salt (EDANS)

A solution of EDANS (35 mg, $1.21\times10^{-4}$ mol in 45 ml deionized water and 3 ml acetonitrile) was adjusted to pH 8.5, and 4 (350 mg) was added. The reaction mixture was stirred at room temperature for 24 hrs and was then centrifuged to collect the powder. The product was washed until the supernatant no longer exhibited significant fluorescence under UV illumination. The washing procedure consisted of suspending the powder in a solution of 0.05M NaOH/methanol (0.15 ml) in 20 ml methanol and manually shaking for 6 minutes. The powder was recovered by centrifugation to yield 8a. To control for non-covalent adsorption of the dye to the particle surface, a control sample was prepared in a similar way by substituting non-activated powder 6b for 7 to yield 8b.

Example 4

Surface Loading of EDANS Dye on 8

Product 8a and control 8b (20 mg) were added separately to 50 ml centrifuge tubes. A sodium hydroxide solution (10.0 ml, pH 7.5) was added, and the samples were placed on a shaker for 24 hrs after which time the samples were centrifuged and fluorescence readings of the supernatant were measured. The supernatant was removed, and fresh pH 7.5 solution was added to remove loosely-bonded fluorophore. Every 24 hrs, the supernatant was removed, fluorescence measurements were taken, and fresh pH 7.5 solution was added, until no significant fluorescence signal was measured in the supernatant. At this point the supernatant was removed and an aqueous solution of NaOH (10.0 ml, 0.1 M, pH 13) was added to hydrolyze the organics from the surface and release the covalently-bound dye into solution. The samples were shaken for 24 hours, after which time they were centrifuged, the supernatant was removed, and fluorescence intensity measurements were taken. Fresh NaOH solution (10.0 ml, 0.1 M, pH 13) was added to each sample, and the samples were shaken for an additional 24 hours to remove any dye that was still bonded to the particles. The samples were then centrifuged, the supernatant was removed, and fluorescence intensity measurements were taken. A linear plot of fluorescence intensity versus concentration was constructed from a set of EDANS calibration standards (130 nM-7 μM in 0.1 M NaOH), and the concentrations of cleaved EDANS dye in the supernatant for each sample was calculated using this linear fit equation. The amount of cleaved EDANS for each sample was then obtained from the calculated concentrations and the volume of the supernatant. The total amount of EDANS for each sample was calculated by adding the amounts of dye cleaved during the first and second 24 hr periods. The surface loading of EDANS dye was then calculated from measured surface area of the particles, the total amount of cleaved EDANS, and the amount of surface-modified particles used for the experiment.

Example 5

In Vitro Adhesion Study

NIH 3T3 cells were maintained in Dulbecco's Modified Eagle's Medium (DMEM) with 10% calf serum (Hyclone) and were prepared for cell adhesion experiments as previously described in Midwood, K. S. et al., Tenascin-C Modulates Matrix Contraction via Focal Adhesion Kinase- and Rho-mediated Signaling Pathways. *Mol. Biol. Cell* 2002, 13, 3601-3613. Cells ($10^4$ cells/ml in Tris buffer), pre-stained with Cell Tracker Green (30 min at 37° C.), were added to tissue culture wells containing peptide-modified pellets pressed from particles of 7, tri(ethylene glycol)-modified pellets pressed from particles of 4b, or unmodified $Y_2O_3$ pellets. Cells were allowed to attach for 90 min after which time non-adherent cells were removed by several washings with Tris buffer. The cells were then fixed (15 min, 3.7% formaldehyde in PBS) and visualized using a Nikon Optiphot-2 microscope. Images were obtained using a Photometrics Coolsnap camera, and image analysis was performed using IPLab software. Quantification of cell adhesion for each surface was assessed by counting the number of cells in randomly-generated microscope fields (10× magnification, minimum of six fields for each type of sample).

Example 6

Synthesis of 5% Europium-Doped $Y_2O_3$ Nanoparticles ($Y_2O_3$:$Eu^{3+}$)

A modification of a literature procedure was used. (Kaczmarek, W. A. et al., *J. Mater. Sci.*, 41, 8320-8328 (2006).) Lanthanide salts $YCl_3.6H_2O$ (0.364 g, 1.2 mmol) and $EuCl_3.6H_2O$ (0.023 g, 0.063 mmol) were dissolved in 100 ml deionized (DI) water in a 250 ml round-bottom flask, and urea (1.44 g, 24 mmol) was added. The pH was adjusted to between 5.5 and 6, and the solution was then heated to 90-100° C. A slight turbidity was visible, and the reaction was allowed to proceed for 90 min. The subsequent white suspension was then cooled by immersing the flask in a water bath; ice was added until the flask reached room temperature. The $Y(OH)CO_3$ nanoparticles were then collected by centrifugation (~5000×g, 40 minutes) and washed four times with 80 ml DI water followed by centrifugation. The particles were air-dried overnight and then dried for 3 hours at 110° C. under vacuum (~0.5 torr). Annealing at 785° C. for 1 hr in air (~2-3 hrs to reach 785° C. and <1 hr cool down) converted the nanoparticles from the yttrium hydroxycarbonate precursor to yttrium oxide. X-ray powder diffraction patterns matched published ones. TEM images indicated particle sizes between 80 and 120 nm.

Example 7

Reaction of 5 with GRGDSPK Peptide

Nanoparticles 5 (12 mg) were suspended in 5 ml deionized water and were added to an aqueous buffer solution (100 mM triethanolamine, 20 ml) containing peptide GRGDSPK (6 mg 80% GRGDSPK, $6.7×10^{-6}$ mol). The reaction mixture was stirred at room temperature for 22 hrs, and the particles were collected by centrifugation. Unreacted p-nitrophenyl carbonate groups on the nanoparticles were passivated by agitating in a Tris-buffered solution (100 mM, pH 8, 20 ml) for 20 min. The particles were then collected by centrifugation and washed twice with pH 7.5 water (20 ml) to obtain 9a.

Example 8

Reaction of 5 with GRADSPK Peptide (Control for 9a)

This reaction used the same procedure as for the synthesis of 9a except that cell-inactive GRADSPK peptide was substituted for cell-attractive GRGDSPK peptide to give 9b.

Example 9

In Vitro Studies of Nanoparticles (Confluent Cell Layer)

NIH 3T3 cells maintained in Dulbecco's Modified Eagle's Medium (DMEM) with 10% calf serum (Hyclone) were prepared for cell adhesion experiments as described above. Cells ($10^5$ cells/ml), pre-stained with Cell Tracker Green (Molecular Probes) were allowed to attach to glass coverslips in DMEM (with serum) for 90 min, after which time the medium was removed and fresh DMEM (970 μl, without serum) was added. Nanoparticles 9a or control 9b (30 μl, 2 mg/ml in Tris buffer) were then added to each well to give a total concentration of 60 μg/ml and were allowed to attach for 3 hrs. The medium was removed, and the cells were washed with phosphate buffered saline (PBS). Cells were then fixed (15 min, 3.7% formaldehyde in PBS) and washed extensively with PBS. Samples were visualized using a Nikon Optiphot-2 microscope and images were obtained with a Photometrics Coolsnap camera and analyzed with IPLab software.

Example 10

In Vitro Studies of Nanoparticles (Non-Confluent Cell Layer)

NIH 3T3 cells maintained in DMEM with 10% calf serum (Hyclone) were prepared for cell adhesion experiments as previously described. Cells ($2×10^4$ cells/ml), prestained with Cell Tracker Green (Molecular Probes) were allowed to attach to glass coverslips in DMEM (with serum) for 90 min, after which time the medium was removed and fresh DMEM (900 μl, without serum) was added. Nanoparticles 9a or control 9b (100 μl, 2 mg/ml in Tris buffer) were then added to each well to give a total concentration of 200 μg/ml and were allowed to attach for 2 hrs. The medium was removed, and the cells were washed with PBS. Cells were then fixed (15 min, 3.7% formaldehyde in PBS) and washed extensively with DI water. Samples were visualized using a Nikon Optiphot-2 microscope and images were obtained with a Photometrics Coolsnap camera and analyzed with IPLab software.

Example 11

Nanoparticle Binding Inhibition Study. NIH 3T3 cells maintained in DMEM with 10% calf serum (Hyclone) were prepared for cell adhesion experiments as previously described. Cells ($10^4$ cells/ml), pre-stained with Cell Tracker Green (Molecular Probes) were allowed to attach to glass coverslips in DMEM (with serum) for 90 min, after which time the medium was removed and fresh DMEM (920 μl, without serum) was added. Nanoparticles 9a (30 μl, 2 mg/ml in Tris buffer) were then added to each well with or without soluble peptide (50 μl, 2.2 mM GRGDSPK in DMEM) to give a total concentration of 60 μg/ml nanoparticles and 0.11 mM peptide (if added); particles were allowed to attach for 2 hrs. The medium was removed, and the cells were washed with PBS. Cells were then fixed (15 min, 3.7% formaldehyde in PBS) and washed extensively with PBS. Samples were visualized using a Nikon Optiphot-2 microscope and images were obtained with a Photometrics Coolsnap camera and analyzed with IPLab software.

Although the present invention has been described in considerable detail with reference to certain versions thereof, other versions are possible. Therefore, the spirit and scope of the appended claims should not be limited to the description of the versions contained herein.

What is claimed is:

1. Nanoparticles having the structure:

wherein R is a covalently attached biomolecule conjugate and M is a nanoparticle selected from the group consisting of lanthanum, yttrium, lead, zinc, cadmium, beryllium, magnesium, calcium, barium, aluminum, radium, silicon and germanium.

2. The nanoparticles of claim 1, the nanoparticle M further comprising ions of one or more rare earth elements.

3. The nanoparticles of claim 2, wherein the rare earth element ions are ions of one or more rare earth elements selected from the group consisting of samarium, gadolinium, lanthanum, yttrium, europium, cerium, terbium, dysprosium, holmium, erbium, thulium, ytterbium and lutetium.

4. The nanoparticles of claim 2, wherein the rare earth ions comprise a combination of ytterbium ions and one or more ions selected from the group consisting of erbium, holmium and thulium ions.

5. The nanoparticles of claim 1, wherein the nanoparticle M comprises an oxide of one or more elements selected from the group consisting of lanthanum, yttrium, lead, zinc, cadmium, magnesium, calcium, barium, aluminum, silicon and germanium.

6. The nanoparticles of claim 1, wherein the nanoparticle M comprises yttrium oxide ($Y_2O_3$).

7. The nanoparticles of claim 1 wherein the nanoparticle M comprises yttrium oxide doped with europium ions.

8. The nanoparticles of claim 6 wherein the nanoparticle M is doped with luminescent europium ions.

9. The nanoparticles of claim 1, wherein the nanoparticles comprise one or more biomolecular probes and the nanoparticle M comprises ions of one or more rare earth elements.

10. The nanoparticles of claim 9, wherein the biomolecular probes are selected from the group consisting of proteins and peptides that bind to biological markers.

11. A method for making a nanoparticle having the structure:

wherein R is a covalently attached biomolecule conjugate and M is a nanoparticle selected from the group consisting of lanthanum, yttrium, lead, zinc, cadmium, beryllium, magnesium, calcium, barium, aluminum, radium, silicon and germanium, comprising attaching on the nanoparticle M an alkyl or aryl phosphonate monolayer having a terminus reactive for cross-coupling, reacting the nanoparticle with a cross-coupling agent appropriate for binding a conjugate to a surface of the nanoparticle, and attaching a biomolecule conjugate operable to bind a receptor of interest.

12. The method according to claim 11 comprising reacting the nanoparticle M with p-nitrophenyl chloroformate to provide a p-nitrophenyl carbonate derivatized nanoparticle that can react with amines.

13. The method according to claim 12 comprising binding tri(ethylene glycol) monoamine to the p-nitrophenyl carbonate derivatized nanoparticle.

14. The method according to claim 11, wherein the nanoparticle M is yttria oxide.

15. The method of claim 11, wherein the nanoparticle M is doped with ions of one or more rare earth elements.

16. The method according to claim 11 wherein the phosphonate monolayer comprises 11-hydroxyundecylphosphonate (PUL).

17. The method according to claim 11 further comprising the step of attaching the nanoparticle to at least one biological molecule.

18. The method of claim 11 wherein the nanoparticle M comprises yttrium oxide doped with europium ions.

19. The method of claim 18 wherein the nanoparticle M is doped with luminescent europium ions.

20. The method of claim 17, wherein the at least one biological molecule comprises one or more biomolecular probes and the nanoparticle M comprises ions of one or more rare earth elements.

21. The method of claim 20, wherein the biomolecular probes are selected from the group consisting of proteins and peptides that bind to biological markers.

22. A tissue imaging method comprising:
(a) labeling tissue to be imaged with the rare earth ion doped nanoparticles according to claim 9, wherein the nanoparticles comprise one or more biomolecular probes that bind to biological markers on said tissue;
(b) exciting the nanoparticles with tissue-penetrating electromagnetic radiation of a wavelength that stimulates the rare earth ions to emit photons; and
(c) converting the photon emission to a visible image.

23. The method of claim 22, wherein the tissue-penetrating radiation capable of stimulating rare-earth ions to emit photons comprises UV, visible or infrared wavelengths.

24. The method of claim 22, wherein the tissue is imaged in-vivo.

25. The method of claim 22, wherein the tissue is imaged ex-vivo.

26. The method of claim 22, wherein the emitted photons comprise infrared or visible wavelengths.

27. In a method for treating diseased tissue in a living being by photodynamic therapy comprising introducing into the body of said living being in proximity to said diseased tissue a photosensitizing agent that generates species toxic to said diseased tissue upon exposure to stimulating wavelengths of electromagnetic radiation, and exposing the photosensitizing agent to electromagnetic radiation of a wavelength that stimulates the photosensitizing agent to generate said toxic species, comprising:
administering to said living being rare earth ion doped nanoparticles according to claim 9.

28. The method of claim 27, wherein the nanoparticle comprises the photosensitizing agent.

29. The method of claim 27, wherein the diseased tissue comprises a malignant tumor.

30. The method of claim 27, wherein the rare earth ions emit photons of a wavelength that stimulates the photosensitizing agent to generate a toxic species upon exposure to tissue-penetrating radiation which comprises UV, visible or infrared wavelengths.

31. The method of claim 27, wherein the rare earth ions emit photons of a wavelength that stimulates the photosensitizing agent to generate a toxic species upon exposure to tissue-penetrating radiation, and wherein the emitted photons comprise infrared or visible wavelengths.

* * * * *

UNITED STATES PATENT AND TRADEMARK OFFICE
CERTIFICATE OF CORRECTION

| | | |
|---|---|---|
| PATENT NO. | : 8,372,435 B2 | |
| APPLICATION NO. | : 12/489242 | |
| DATED | : February 12, 2013 | |
| INVENTOR(S) | : Jeffrey Schwartz, Christopher Traina and Thomas J. Dennes | |

It is certified that error appears in the above-identified patent and that said Letters Patent is hereby corrected as shown below:

In the Specifications

Column 1, Lines 16-20 under the title STATEMENT REGARDING FEDERALLY SPONSORED RESEARCH should read:

This invention was made with government support under Grant No. CHE-0612572 awarded by the National Science Foundation. The government has certain rights in the invention.

Signed and Sealed this
Sixteenth Day of July, 2013

Teresa Stanek Rea
*Acting Director of the United States Patent and Trademark Office*